US011154982B2

(12) United States Patent
Jackson et al.

(10) Patent No.: US 11,154,982 B2
(45) Date of Patent: Oct. 26, 2021

(54) ATTACHMENT STRUCTURE FOR SECURING A ROBOT ARM TO A SUPPORT STRUCTURE

(71) Applicant: CMR Surgical Limited, Cambridge (GB)

(72) Inventors: Thomas Bates Jackson, Cambridge (GB); Keith Marshall, Cambridge (GB)

(73) Assignee: CMR SURGICAL LIMITED, Cambridge (GB)

( * ) Notice: Subject to any disclaimer, the term of this patent is extended or adjusted under 35 U.S.C. 154(b) by 307 days.

(21) Appl. No.: 16/348,101

(22) PCT Filed: Nov. 7, 2017

(86) PCT No.: PCT/GB2017/053347
§ 371 (c)(1),
(2) Date: May 7, 2019

(87) PCT Pub. No.: WO2018/087531
PCT Pub. Date: May 17, 2018

(65) Prior Publication Data
US 2019/0308312 A1    Oct. 10, 2019

(30) Foreign Application Priority Data
Nov. 8, 2016   (GB) ..................... 1618840

(51) Int. Cl.
*B25J 9/00*   (2006.01)
*A61B 34/30*   (2016.01)
(Continued)

(52) U.S. Cl.
CPC ............. *B25J 9/0009* (2013.01); *A61B 34/30* (2016.02); *A61B 34/70* (2016.02); *B25J 18/00* (2013.01); *A61B 2090/571* (2016.02)

(58) Field of Classification Search
CPC .. B25J 9/0009; B25J 9/08; B25J 19/00; A61B 34/30; A61B 34/70
See application file for complete search history.

(56) References Cited

U.S. PATENT DOCUMENTS 9,630,315 B2 * 4/2017 Cookson ................ B25J 9/1612
2010/0012798 A1   1/2010 Blum et al.
(Continued)

FOREIGN PATENT DOCUMENTS

DE   10 2012 110193    4/2014
WO   WO 2014/0139010   9/2014
(Continued)

OTHER PUBLICATIONS

Stephane Husselin, International Search Report issued in application PCT/GB2017/053347, completion date Feb. 1, 2018 dated Feb. 9, 2018, 3 pages.
Colin Powys, Search Report issued in application No. GB1618840.1, dated Mar. 20, 2017, 1 page.
Machine Translation of DE 10 2012 110193 via Google Patents, May 7, 2019, 7 pages.

*Primary Examiner* — Bobby Rushing, Jr.
(74) *Attorney, Agent, or Firm* — King & Spalding LLP (57) ABSTRACT

An attachment structure for securing a robot arm to a support structure, the attachment structure comprising: a mount for mounting to the support structure; and a carrier for connecting to the base of the robot arm, the carrier comprising: a carrier rotational alignment feature for engaging a complementary robot arm base rotational alignment feature, a carrier axial alignment feature for engaging a complementary robot arm base axial alignment feature, and a locking mechanism moveable, once the robot arm base and the carrier are engaged, between an unlocked position which does not constrain the location of the robot arm base along an axis of the carrier, and a locked position which does constrain the location of the robot arm base along the said axis of the carrier relative to the carrier, wherein the locking mechanism is independent of the carrier rotational alignment (Continued)

feature and the carrier axial alignment feature such that the locking mechanism is not actuated during engagement of the carrier and the robot arm base.

19 Claims, 10 Drawing Sheets

(51) Int. Cl.
*B25J 18/00* (2006.01)
*A61B 34/00* (2016.01)
*A61B 90/57* (2016.01)

(56) References Cited

U.S. PATENT DOCUMENTS

| | | |
|---|---|---|
| 2011/0257786 A1 | 10/2011 | Caron L'Ecuyer et al. |
| 2014/0005705 A1* | 1/2014 | Weir ................. A61B 18/08 606/169 |
| 2016/0184037 A1* | 6/2016 | Cooper ............... A61B 34/30 606/130 |
| 2017/0086930 A1* | 3/2017 | Thompson ........... A61B 34/30 |

FOREIGN PATENT DOCUMENTS

| | | |
|---|---|---|
| WO | WO 2017/083253 | 5/2017 |
| WO | WO 2017/098278 | 6/2017 |

\* cited by examiner

ATTACHMENT STRUCTURE FOR SECURING A ROBOT ARM TO A SUPPORT STRUCTURE

BACKGROUND

Surgical robots can be used to perform some minimally invasive surgical operations which would otherwise be performed by manual laparoscopy. The same surgical robot arm can be fitted with different surgical instruments (grippers, scalpel, cauteriser etc) enabling it to perform different procedures at a surgical site inside a patient. Typically, several implements are utilised simultaneously at the surgical site, for example grippers, scalpel and an endoscope, each of which may be supported by a different robot arm.

The location of the surgical site and the access to that surgical site depends on the specific operation being undertaken. Thus, the location of the surgical robot is dependent on the specific operation being undertaken. For some operations, the surgical robot may ideally be located on the ceiling and extend down for access to the surgical site via, for example, the throat. For other operations, the surgical robot may ideally be located on the floor or on the patient's table rail. The surgical robot may ideally be located in one position for a first period of the operation and then moved to another position. This may be achieved by locating the surgical robot on a moveable cart.

It is known to install the surgical robot arms to be used in an operation on a common chassis. This setup is limiting since all the robot arms in the operation must extend from the same base. This arrangement does not enable different robot arms to be located in different places around the operating room, thus does not enable optimal robot arm placement. This arrangement also does not enable the operating staff themselves to have optimal access to the patient since they must manoeuvre around the robot arms.

It is also known to use cart-mounted robot arms. Separately, it is known to mount the surgical robot arms to the patient's table rails. These systems are more flexible than installing the robot arms on a common chassis, but still only provide a limited range of locations that the robot can be placed in in the operation room. For example, neither of these systems enables a robot arm to be installed on the ceiling.

There is a need for a system for installing surgical robots in an operating room which provides more flexibility of the locations at which the surgical robot arm is able to be installed in the operating room. There is also a need for a system which enables a surgical robot arm to be more easily and quickly relocated from one position to another in the operation room during an operation.

SUMMARY OF THE INVENTION

According to an aspect of the invention, there is provided an attachment structure for securing a robot arm to a support structure, the attachment structure comprising: a mount for mounting to the support structure; and a carrier for connecting to the base of the robot arm, the carrier comprising: a carrier rotational alignment feature for engaging a complementary robot arm base rotational alignment feature, a carrier axial alignment feature for engaging a complementary robot arm base axial alignment feature, and a locking mechanism moveable, once the robot arm base and the carrier are engaged, between an unlocked position which does not constrain the location of the robot arm base along an axis of the carrier, and a locked position which does constrain the location of the robot arm base along the said axis of the carrier relative to the carrier, wherein the locking mechanism is independent of the carrier rotational alignment feature and the carrier axial alignment feature such that the locking mechanism is not actuated during engagement of the carrier and the robot arm base.

The carrier may comprise a plurality of carrier rotational alignment features for engaging complementary robot arm base rotational alignment features, wherein the plurality of carrier rotational alignment features are rotationally asymmetric so as to only engage the complementary robot arm base rotational alignment features in one relative rotational configuration of the carrier and robot arm base.

The carrier rotational alignment feature(s) may be recesses for receiving corresponding projections of the robot arm base. Each recess may comprise at least one protrusion for securing the robot arm base in the recess.

The carrier rotational alignment feature(s) may be roller bearings for being received in corresponding recesses of the robot arm base.

The carrier may comprise a plurality of further carrier rotational alignment features for engaging complementary further robot arm base rotational alignment features. Each further carrier rotational alignment feature may be a roller bearing having a rotation axis perpendicular to the carrier's longitudinal axis, and having a roller surface configured to contact the further robot arm base rotational alignment feature so as to aid axial movement of the robot arm base against the carrier during engagement.

The carrier may comprise two sets of roller bearings, a first set arranged in a first annulus perpendicular to the carrier's longitudinal axis, and a second set arranged in a second annulus perpendicular to the carrier's longitudinal axis, the first and second annuli being separated in the direction of the carrier's longitudinal axis.

The attachment structure may further comprise rotational alignment indicators visible from the exterior of the carrier for indicating a relative orientation of the carrier and the robot arm base.

The carrier may comprise a plurality of carrier axial alignment features for engaging complementary robot arm base axial alignment features.

The carrier axial alignment feature(s) may be rings centred on the carrier's longitudinal axis for engaging corresponding rings of the robot arm base. The attachment structure may comprise two rings centred on the carrier's longitudinal axis, the two rings separated in the direction of the carrier's longitudinal axis. Each ring may comprise a flange for seating a corresponding robot arm base axial alignment feature.

The locking mechanism may be compressible between a compressed state in the unlocked position such that no force is applied to the robot arm base by the locking mechanism, and an uncompressed state in the locked position such that force compressing the robot arm base and carrier together is applied to the robot arm base by the locking mechanism.

The locking mechanism may comprise a collar rotatable about the carrier's longitudinal axis, the collar being compressible in the direction of the carrier's longitudinal axis between a compressed state in the unlocked position such that no force in the direction of the carrier's longitudinal axis is applied to the robot arm base by the collar, and an uncompressed state in the locked position such that force in the direction of the carrier's longitudinal axis compressing the robot arm base and carrier together is applied to the robot arm base by the collar.

The locking mechanism may comprise a wing compressible between a compressed state in the unlocked position such that no force transverse to the carrier's longitudinal axis is applied to the robot arm base by the wing, and an uncompressed state in the locked position such that force transverse to the carrier's longitudinal axis is applied to the robot arm base by the wing.

In the locked position of the locking mechanism, the carrier rotational alignment feature may be immovable relative to the robot arm base rotational alignment feature and the carrier axial alignment feature may be immovable relative to the robot arm base axial alignment feature.

The face of the collar which contacts the robot arm base may be shaped so as to increasingly bear down on the robot arm base as the collar is rotated from its unlocked position to its locked position.

The face of the collar may comprise an initial detent and a final detent located such that as the collar begins to be rotated from its unlocked position to its locked position the initial detent bears down on the robot arm base, and the collar reaches the locked position just after the final detent bears down on the robot arm base.

The collar may comprise an outer grip part and a compression part separated by a spring washer, all constrained to rotate together about the carrier's longitudinal axis.

The compression part may comprise the face of the collar which contacts the robot arm base. The compression part may move relative to the outer grip part parallel to the carrier's longitudinal axis as the collar is rotated between the unlocked position and the locked position.

The collar may be rotatable about the carrier's longitudinal axis between the unlocked position and an ejected position. The collar may further comprise an ejection mechanism configured to apply force to the robot arm base in the direction of the carrier's longitudinal axis prising the robot arm base and carrier apart as the collar is rotated from the unlocked position to the ejected position.

The ejection mechanism may comprise one or more wedge-shaped projections which engage one or more complementary robot arm base features.

The one or more wedge-shaped projections may engage a robot arm base rotational alignment feature.

The collar may comprise a marking which is only visible in either the compressed state or the uncompressed state.

The carrier may comprise a hollow opening configured to encompass the robot arm base when engaged.

The carrier may comprise one or more carrier supporting feature for engaging one or more complementary robot arm base supporting feature.

The carrier supporting feature may comprise a groove on an interior surface of the carrier, the groove being in a plane transverse to the longitudinal axis of the carrier.

The groove may comprise one or more detent for receiving a robot arm base supporting feature.

The carrier may have a circular cross-section. The carrier may be rigidly attached to the mount.

The mount may comprise a mounting surface for interfacing a surface of the support structure, wherein the mounting surface is not perpendicular to the carrier's longitudinal axis.

The mounting surface may be at an angle of 45° to the carrier's longitudinal axis.

The mount may comprise an aperture for enabling a cable connection to the robot arm base.

The mount may comprise electrical connectors configured to connect to the robot arm base and an external apparatus.

According to a further aspect of the invention, there is provided a surgical robot comprising a robot arm base connected to an attachment for a surgical instrument via a series of articulated links, the robot arm base suitable for being secured to a support structure via a carrier, the robot arm base comprising: a robot arm base rotational alignment feature for engaging a complimentary carrier rotational alignment feature; and a robot arm base axial alignment feature for engaging a complimentary carrier axial alignment feature.

The robot arm base may comprise a plurality of robot arm base rotational alignment features for engaging complimentary carrier rotational alignment features, wherein the plurality of robot arm base rotational alignment features are rotationally asymmetric so as to only engage the complementary carrier rotational alignment features in one relative rotational configuration of the carrier and the robot arm base.

The robot arm base rotational alignment feature(s) may be roller bearings for being received in corresponding recesses of the carrier.

The robot arm base rotational alignment feature(s) may be recesses for receiving corresponding projections of the carrier.

The robot arm base may comprise a plurality of further robot arm base rotational alignment features for engaging complementary further carrier rotational alignment features.

Each further robot arm base rotational alignment feature may be a raised flat surface configured to contact the further carrier rotational alignment feature so as to aid axial movement of the robot arm base against the carrier during engagement.

The robot arm base may comprise a plurality of robot arm base axial alignment features for engaging complementary carrier axial alignment features.

The robot arm base axial alignment feature(s) may be rings centred on the robot arm base's longitudinal axis for engaging corresponding rings of the carrier. Two rings may be centred on the robot arm base's longitudinal axis, the two rings separated in the direction of the robot arm base's longitudinal axis.

Each ring may comprise a flange for engaging a complementary flange of a corresponding carrier axial alignment feature.

The surgical robot may further comprise one or more robot arm base supporting feature for engaging complementary one or more carrier supporting feature. The robot arm base supporting features may comprise spring roller bearings.

BRIEF DESCRIPTION OF THE FIGURES

The present invention will now be described by way of example with reference to the accompanying drawings. In the drawings.

DETAILED DESCRIPTION

The following describes an attachment structure for securing a robot arm to a support structure. The support structure may be fixed, such as the floor, ceiling or wall. Alternatively, the support structure may be moveable, such as a cart or ceiling mounted linkage. Once installed, the attachment structure is securely attached to the support structure. Similarly, once installed, the robot arm is securely attached to the attachment structure. Once engaged and locked together, the attachment structure constrains the robot arm such that there is no movement of the robot arm relative to the attachment structure. This ensures no error is introduced into the control system's control of the movement of the end effector by the robot arm base moving. It also provides a stable base for the robot arm to react against in providing forces to the surgical instrument. The attachment structure described provides this stability and security whilst also being easy to attach to the support structure and robot arm by an individual user acting alone. The attachment structure is relatively small and of minimal complexity compared to known mechanisms for installing robot arms in operating theatres. Because of this, several attachment structures may be installed in the operating theatre during pre-operative set up. Robot arms are then installed into the attachment structures as required, and, if required, detached from one attachment structure and installed in another attachment structure during the course of an operation.

Figure 1:
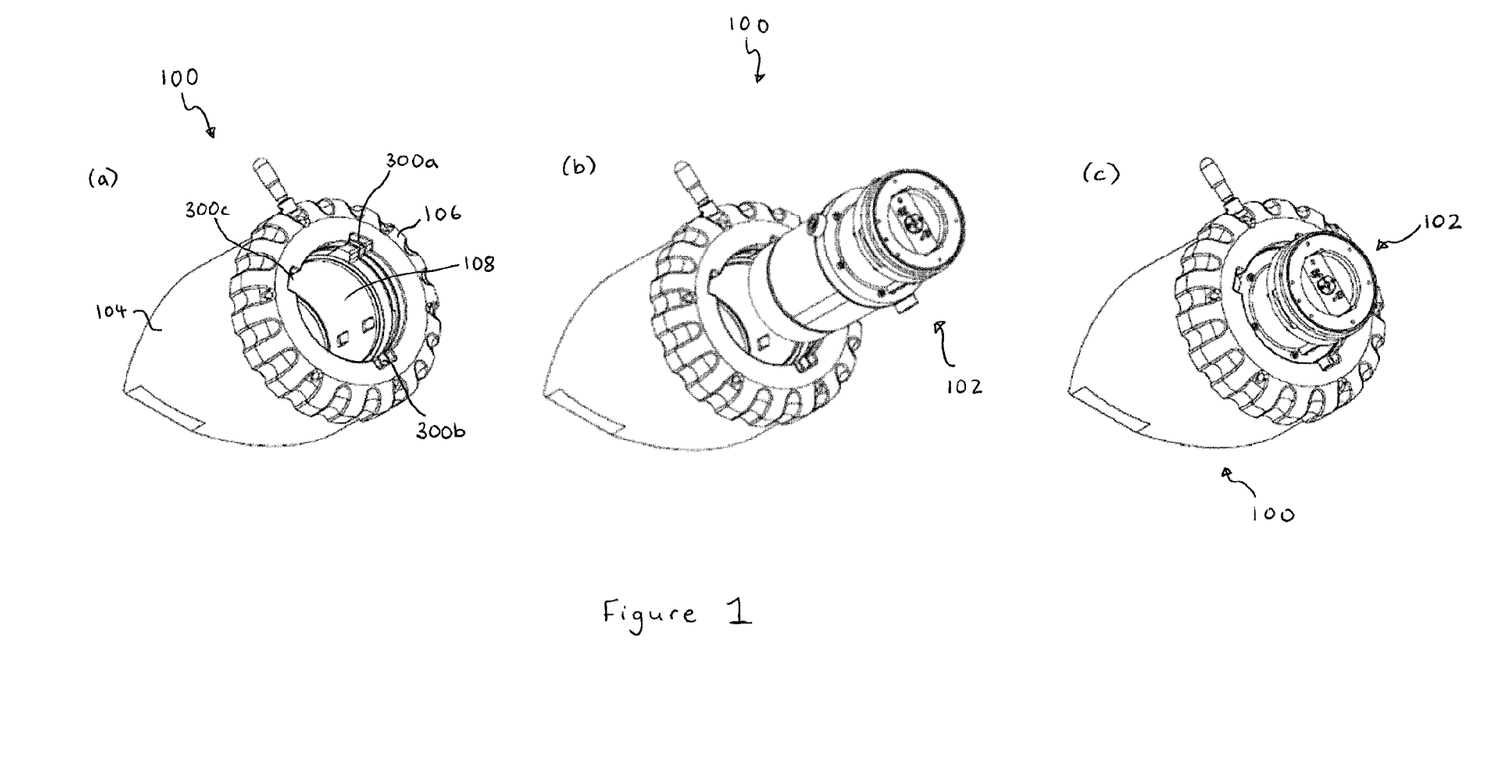
FIGS. 1a, 1b and 1c illustrate an exemplary robot arm base and attachment structure in different stages of engagement.

FIG. 1 illustrates an exemplary implementation of the attachment structure. FIG. 1a illustrates the attachment structure 100 in isolation. FIG. 1b illustrates the robot arm base 102 being brought into engagement with the attachment structure 100. The robot arm comprises a series of articulated links which connect the robot arm base to an attachment for a surgical instrument. The surgical instrument attaches to the final link of the robot arm most distal from the robot arm base. The surgical instrument comprises a shaft and an articulated end effector attached to the end of the shaft most distal from the final link of the robot arm. The figures only illustrate the robot arm base. The remainder of the robot arm has not been shown for ease of illustration. FIG. 1c illustrates the robot arm base 102 installed in the attachment structure 100.

Figure 2:
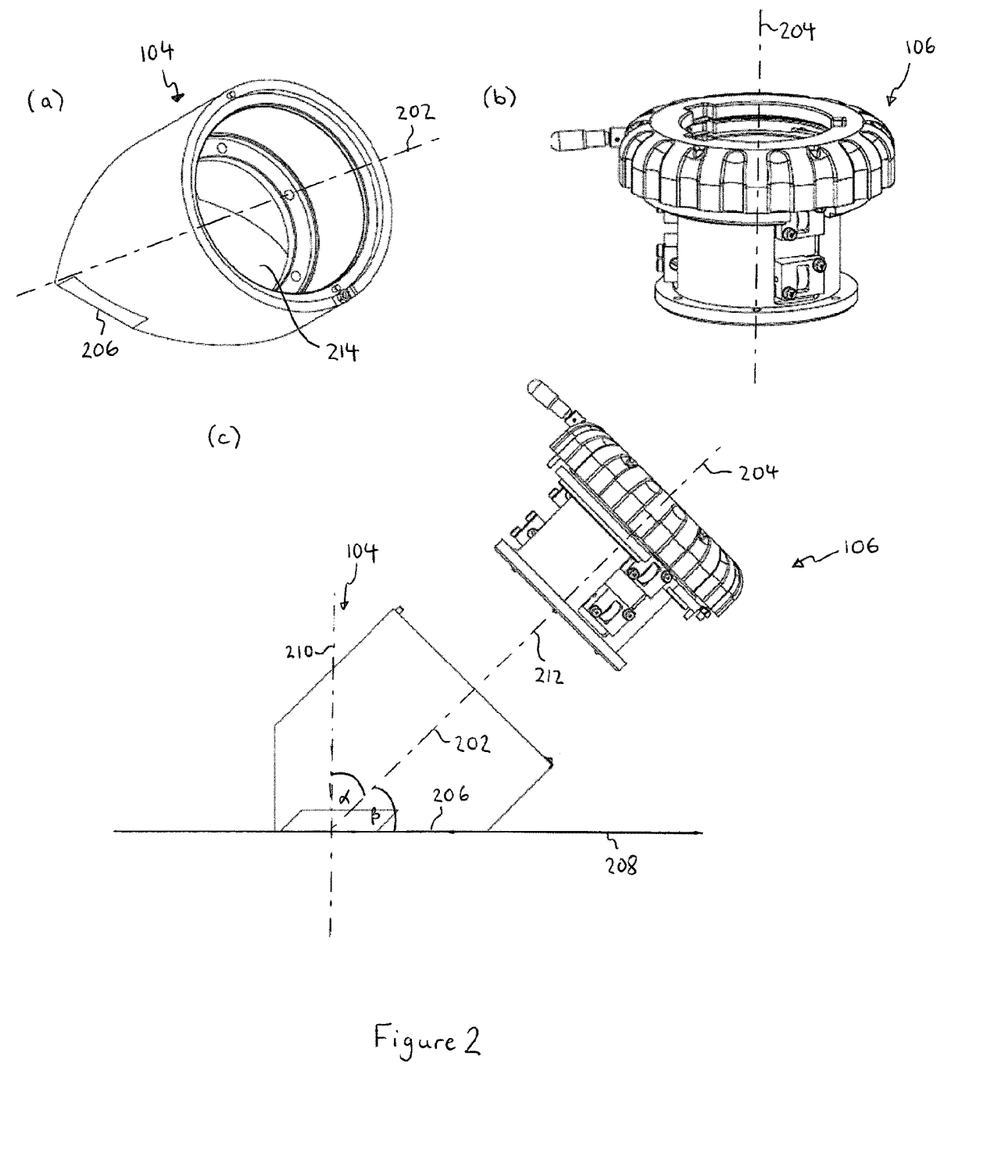
FIGS. 2a, 2b and 2c illustrate the mount and carrier portions of the attachment structure.

The attachment structure comprises two portions: a mount 104 for mounting to the support structure; and a carrier 106 for connecting to the robot arm base. These two portions may be manufactured as two subassemblies, as shown in FIG. 2. The mount 104 is shown in isolation in FIG. 2a. The carrier 106 is shown in isolation in FIG. 2b. An exploded view of the mount 104 and carrier 106 is shown in FIG. 2c. The carrier 106 is rigidly attached to the mount 104. The longitudinal axis of the mount 202 is aligned with the longitudinal axis of the carrier 204. The longitudinal axis of the mount 202 is coincident with the longitudinal axis of the carrier 204.

The mount comprises a mounting surface 206 which interfaces the surface of the support structure 208 to which it mounts. The mounting surface 206 has a complementary shape to the shape of the support structure to which it mounts. This maximises the contact area between the mounting surface 206 and the support structure. In the example illustrated in the figures, this mounting surface 206 is flat, for mounting to, for example, a table 208. Alternatively, the mounting surface 206 may be curved, for example for mounting to a bed rail. The mounting surface 206 may have surface features to aid alignment and/or secure fixing to the support structure. These surface features may be any of studs, protrusions, hooks, clips and/or recesses. These surface features may complement surface features of the support structure. The attachment structure may be mounted at any angle to the support structure. Usefully, the attachment structure is mounted to the support structure such that the longitudinal axis of the attachment structure 212 is not perpendicular 210 to the support structure's surface. In the figures, the mount is shaped such that the longitudinal axis of the attachment structure 212 is at an angle α to the perpendicular of the surface of the support structure 208, and an angle β to the surface of the support structure 208. For example, $30°<\beta<60°$. For example, $40°<\beta<50°$. For example, β may be 45°. Choosing $\alpha \neq 0$ aids the manoeuvrability of the robot arm.

As can be seen in FIGS. 1 and 2, the carrier has a generally cylindrical profile, with a generally circular cross-section. The carrier is generally socket-shaped for receiving a plug-shaped robot arm base. Alternatively, the carrier may be plug-shaped for being received in a socket-shaped robot arm base. In this case, the rotational alignment features, axial alignment features and locking mechanism of the carrier described in the following would instead be located on the robot arm base, and the rotational alignment features and axial alignment features of the robot arm base would instead be located on the carrier.

The carrier has a hollow interior, with an aperture 108 at the end distal from the mount for receiving the robot arm base. When the robot arm base is installed in the carrier, the carrier encompasses the robot arm base, as can be seen in FIG. 1c. In addition to being open-ended at the end of the carrier which receives the robot arm base, the attachment structure may also have an aperture 214 at the opposing end of the attachment structure. This aperture 214 enables an external cable to connect to the robot arm base. This cable connection may provide electrical and/or data connection to the robot arm. Alternatively, the opposing end of the attachment structure may have a closed end, i.e. not comprise an aperture. In this case, that opposing end may comprise electrical connectors. These electrical connectors may have exposed contacts which engage automatically with complementary contacts on the robot arm base when the robot arm base is installed in the carrier. For example, these internal electrical connectors may be built-in quick connectors. The attachment structure connects its internal electrical connectors to electrical connectors on the external surface of the attachment structure. These external electrical connectors are capable of connecting to an external apparatus. The attachment structure thereby routes the electrical/data connection through from the external apparatus to the robot arm and vice versa.

The carrier comprises rotational alignment features which engage complementary rotational alignment features on the robot arm base. These rotational alignment features ensure the robot arm base is rotationally aligned with the attachment structure when installed. There may be just one carrier rotational alignment feature and one corresponding robot arm base rotational alignment feature. Alternatively, there may be a plurality of carrier rotational alignment features and a plurality of robot arm base rotational alignment features.

Figure 3:
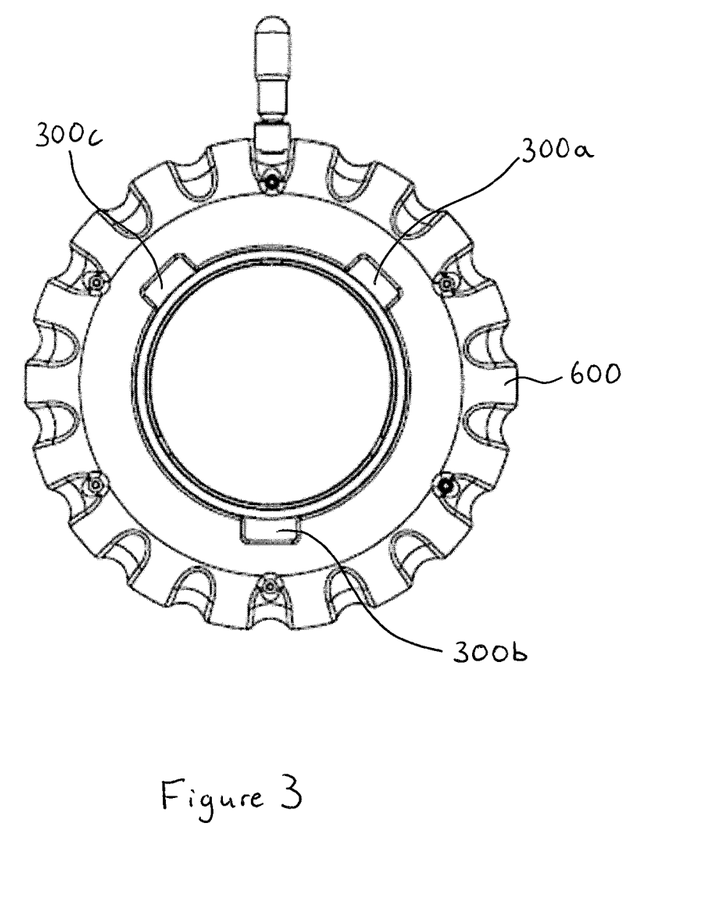
FIG. 3 illustrates an end-on view of the end of the carrier which engages with the robot arm base.

The carrier illustrated in the figures comprises three carrier rotational alignment features. These are illustrated most clearly in FIG. 3, which shows an end-on view of the end of the carrier which engages with the robot arm base. The carrier rotational alignment features are recesses 300a, 300b, 300c, which are exposed at the end of the carrier which engages the robot arm base. The recesses 300a, 300b, 300c partially extend down the internal wall of the carrier, as can be seen in FIG. 1a. The recesses extend parallel to each other and to the longitudinal axis of the carrier down the internal surface of the carrier. Although three recesses are illustrated, the carrier may comprise more or fewer than three recesses.

Figure 4:
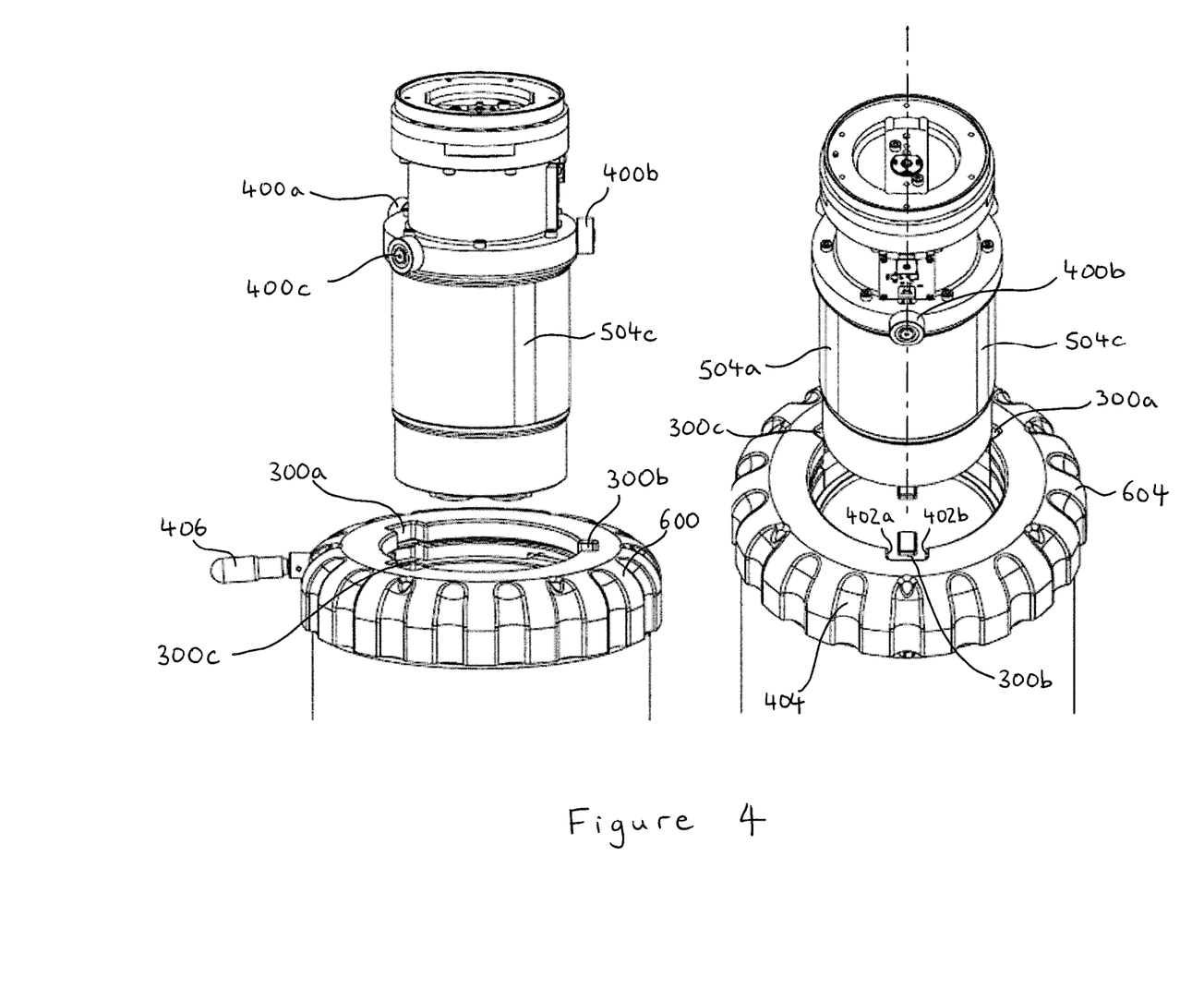
FIG. 4 illustrates an exploded view of the robot arm base and attachment structure.

The robot arm base illustrated in the figures comprises three robot arm base rotational alignment features. These are illustrated in FIG. 4. The robot arm base rotational alignment features are roller bearings 400a, 400b, 400c. Each roller bearing is received in a recess 300a, 300b, 300c of the carrier. Each roller bearing is mounted on a spigot which extends perpendicularly from the exterior side surface of the robot arm base. The roller bearing rotates about the spigot. The roller bearings may be sprung. Although three roller bearings are illustrated, the robot arm base may comprise more or fewer than three roller bearings.

The recesses, or slots, are distributed asymmetrically around the end of the carrier. The roller bearings are arranged in the same asymmetric configuration around the robot arm base. This ensures that the robot arm base can only be installed into the carrier in a single relative rotational orientation. This orientation is such that roller bearing 400a is received in recess 300a, roller bearing 400b is received in recess 300b, and roller bearing 400c is received in recess 300c. The roller bearings are a snug fit in the recesses. The surface of each roller bearing may be in contact with the side walls 402a, 402b of the recess. As the roller bearings are received in the recesses, they roll down the side walls of the recesses, thereby aiding closing axial movement of the robot arm base and the carrier. The recesses retain the roller bearings. Thus, once the roller bearings are received in the recesses, the robot arm base is constrained from rotating relative to the carrier.

Figure 8:
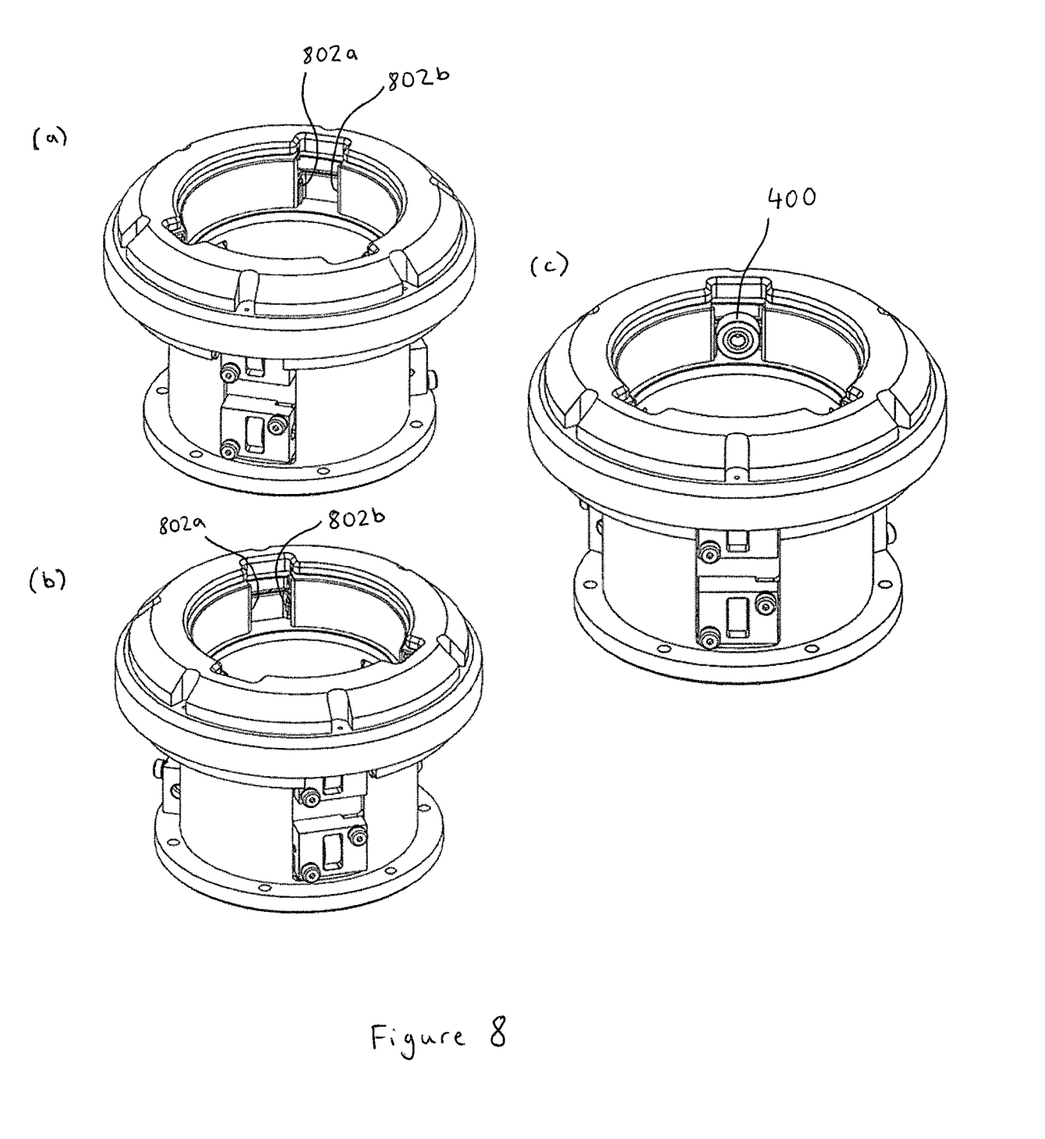
FIGS. 8a, 8b and 8c illustrate the carrier.
Figure 9:
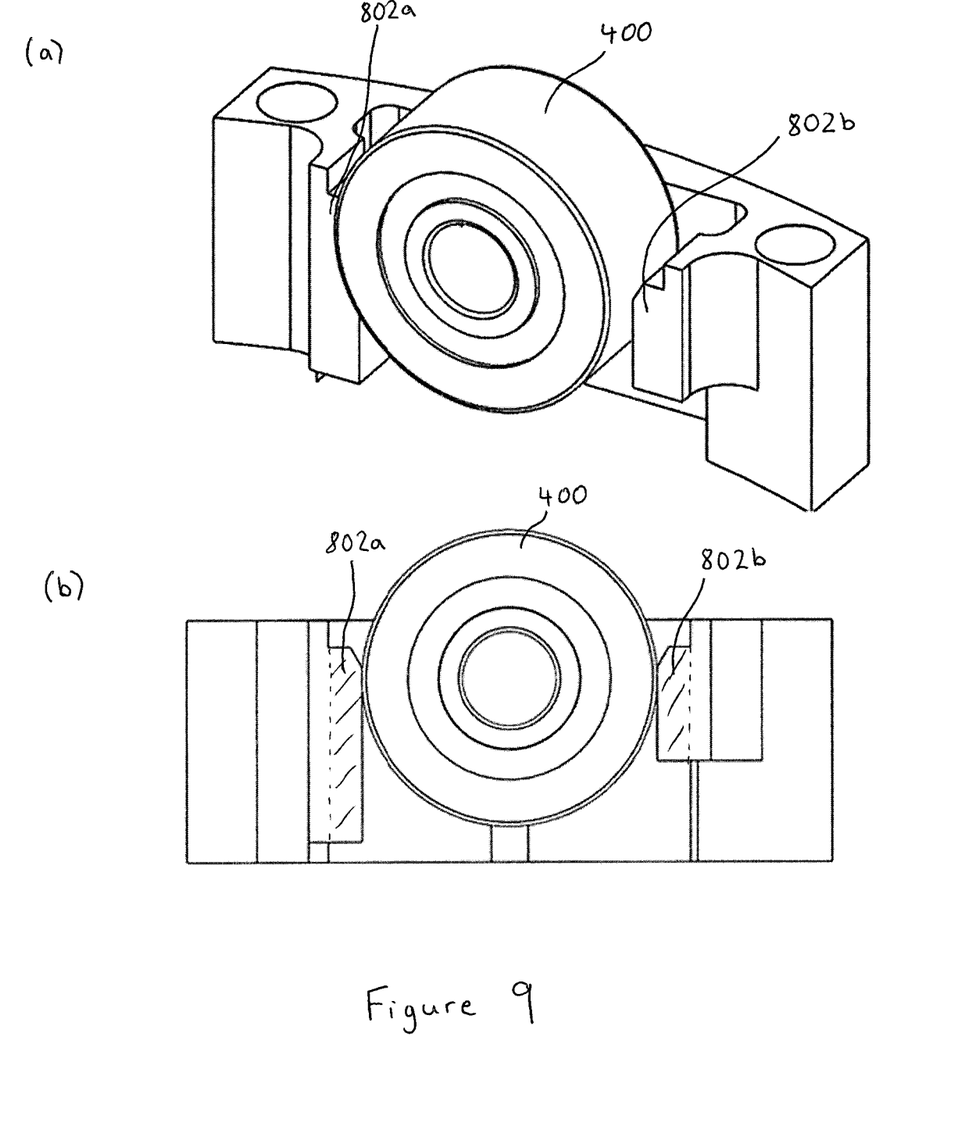
FIGS. 9a and 9b illustrate the seating of a robot arm base roller bearing in a recess of the carrier.

The side walls 402a, 402b of the recess may also comprise one or more protrusion 802a, 802b, most clearly shown on FIGS. 8 and 9. Each protrusion extends out from the side wall in the direction of the roller bearing 400. There may be a protrusion extending out from each of the opposing side walls 402a, 402b of the recess. The protrusion(s) act to narrow the width of the recess. The protrusion(s) are sized such that the spacing between the protrusions matches the width of the roller bearing 400. This aids the snug fit of the roller bearing in the recess. The protrusion(s) thereby more securely retain the roller bearing 400 in the recess.

As an alternative to the roller bearings, the robot arm base rotational alignment features may be raised projections which are retained in the carrier recesses 300a, 300b, 300c. For example, the robot arm base rotational alignment features may be ridges or studs. The raised projection is a snug fit in the carrier recess. This ensures that when the raised projection is received in the recess, the robot arm base is constrained from rotating relative to the carrier.

In an alternative arrangement, the robot arm base rotational alignment features may be recesses as described above, and the carrier rotational alignment features may be roller bearings or raised projections as described above.

Further carrier rotational alignment features may include; a key feature in one of the robot arm base and carrier which slots into a slot feature in the other of the robot arm base and carrier; and/or a peg feature in one of the robot arm base and carrier which slots into a hole feature in the other of the robot arm base and carrier. Both of these features act to secure the robot arm base to the carrier so as to constrain the robot arm base and carrier from any relative rotational movement.

Figure 5:
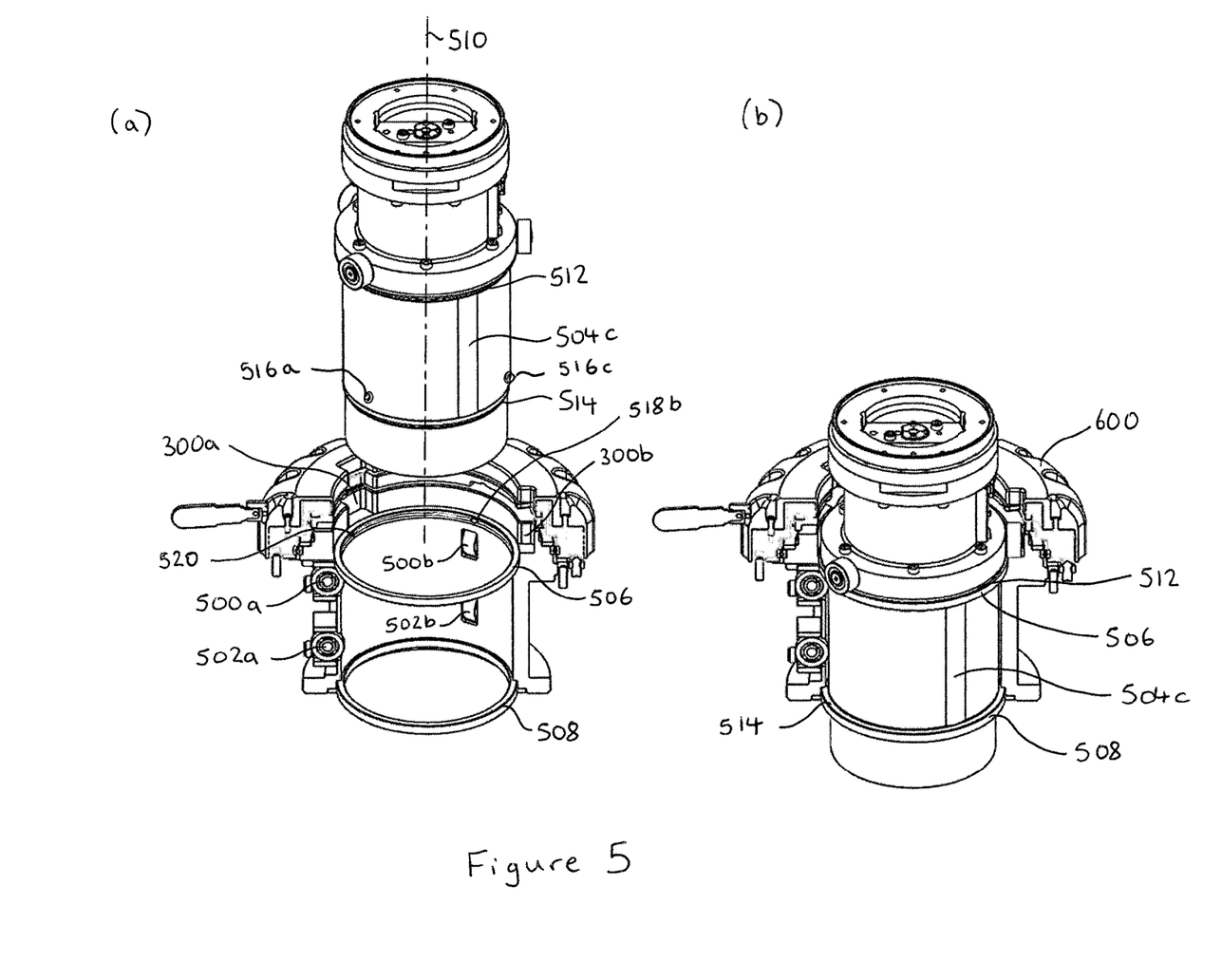
FIGS. 5a and 5b illustrate a cut-away view of the interior of the attachment structure with and without the robot arm base engaged.

The carrier may comprise further rotational alignment features which engage complementary further robot arm base rotational alignment features. FIG. 5 illustrates further carrier rotational alignment features which are roller bearings 500, 502 located on the interior wall of the carrier. Each roller bearing has a rotation axis perpendicular to the carrier's longitudinal axis. Each roller bearing has a roller surface which rotates about the rotation axis. The roller surface is exposed at the interior wall of the carrier. Each roller bearing may be sprung. A first set of three roller bearings 500a, 500b and 500c is arranged in a first annulus perpendicular to the carrier's longitudinal axis. Although three roller bearings are illustrated, more or fewer roller bearings may be used. In the figure, the three roller bearings are equally spaced about the annulus. In an alternative arrangement, the constituent roller bearings of the first set may be distributed unevenly about the annulus. A second set of three roller bearings 502a, 502b, 502c is arranged in a second annulus perpendicular to the carrier's longitudinal axis. Although three roller bearings are illustrated, more or fewer roller bearings may be used. In the figure, the three roller bearings are equally spaced about the annulus. In an alternative arrangement, the constituent roller bearings of the first set may be distributed unevenly about the annulus. The roller bearings of the first set are arranged in the same distribution about the first annulus as the roller bearings of the second set are arranged about the second annulus. Thus, each roller bearing of the first set is aligned in the longitudinal direction of the carrier with a roller bearing of the second set. The first and second annuli are separated in the direction of the carrier's longitudinal axis. The second set of roller bearings is optional. Further sets of roller bearings may additionally be used.

The further robot arm base rotational alignment features illustrated in the figures are raised flat surfaces 504 on the exterior side surface of the robot arm base. The raised flat surfaces 504 are arranged in the same orientation about the robot arm base as the roller bearings are about the carrier. Thus, the raised flat surfaces 504 may be equally spaced about the robot arm base. Each raised flat surface may be elongate, straight, and run parallel to the longitudinal axis of the robot arm base 510. Each raised flat surface 504 contacts a roller bearing of each set of roller bearings of the carrier. In the figures, the raised flat surface 504a contacts roller bearings 500a and 502a. Raised flat surface 504b contacts roller bearings 500b and 502b. Raised flat surface 504c contacts roller bearings 500c and 502c.

The roller surface of a roller bearing of the carrier contacts a raised flat surface of the robot arm base (where the roller surface is exposed at the interior wall of the carrier) as the robot arm base is inserted into the carrier. As the roller surface rotates, it encourages axial movement of the robot arm base into the carrier.

The carrier and robot arm base comprise complementary axial alignment features. These axial alignment features ensure that the robot arm base is fully inserted into the carrier in the direction of the longitudinal axes of the carrier and robot arm base before the robot arm base and carrier are locked together. The carrier axial alignment features may be one or more annular rings centred on the carrier's longitudinal axis. FIG. 5a illustrates two annular rings 506, 508 which protrude from the interior surface of the carrier. The two rings are spaced apart in the direction of the carrier's longitudinal axis. The sets of roller bearings of the carrier may all be located between the two rings 506, 508 in the axial direction of the carrier. One ring 506 may be located proximal to the end of the carrier which first receives the robot arm base. One ring 508 may be located distal from the end of the carrier which first receives the robot arm base.

The robot arm base axial alignment features may be one or more annular rings centred on the robot arm base's longitudinal axis 510. FIG. 5a illustrates two annular rings 512, 514 which protrude from the exterior side surface of the robot arm base. The two rings are spaced apart in the direction of the robot arm base's longitudinal axis 510. The raised flat surfaces 504 may be located between the two rings 512, 514 in the axial direction of the robot arm base. The axial separation of the two rings 512, 514 is the same as the axial separation of the two rings 506, 508.

When the robot arm base is fully inserted into the carrier, the rings of the robot arm base engage with the rings of the carrier. Specifically, in the arrangement shown in the figures, robot arm base ring 512 engages carrier ring 506, and robot arm base ring 514 engages carrier ring 508. The engaging ring pairs have a snug fit. This close sliding fit constrains the rings from moving radially with respect to each other. In other words, it constrains the robot arm base and carrier from relative movement perpendicular to the longitudinal axes of the robot arm base and carrier.

The robot arm base ring 512 most distal from the end of the robot arm base may have a flange. The flange aids seating of the robot arm base ring 512 axially on the carrier ring 506. The carrier ring 506 may have a complementary shaped flange onto which the flange of the robot arm base ring 512 seats. The robot arm base ring 514 may additionally have a flange. This flange aids seating of the robot arm base ring 514 axially on the carrier ring 508. The carrier ring 508 may have a complementary shaped flange onto which the flange of the robot arm base ring 514 seats.

The rings on the robot arm base may be fabricated from steel. The rings on the carrier may be fabricated from brass, such as phosphor brass. A steel ring engaging a brass ring is a hard wearing but lubricious combination.

The rings 512, 514 are positioned on the exterior surface of the robot arm base in such a location that when the rings of the robot arm base engage with the corresponding rings of the carrier, the robot arm base and the carrier are fully engaged and the locking mechanism can be locked. Similarly, the rings 506, 508 are positioned on the interior surface of the carrier in such a location that when the rings of the carrier engage with the corresponding rings of the robot arm base, the robot arm base and the carrier are fully engaged and the locking mechanism can be locked.

The carrier may comprise supporting features which engage complementary supporting features of the robot arm base. These features engage each other when the robot arm base is partially inserted into the carrier. Once the supporting features are engaged, a portion of the weight of the robot arm is borne by the attachment structure. Whilst the supporting features are engaged, the robot arm base and carrier are permitted to rotate relative to each other about the longitudinal axis of the carrier.

The robot arm may be too heavy for a single user to comfortably hold for long. Additionally, the robot arm may be of an awkward shape which delays the time taken for the user to rotationally align the robot arm base and carrier. Thus, it is preferable for the user to not have to rotationally align the robot arm base and carrier whilst bearing the whole weight of the robot arm. However, once the robot arm base is mostly inserted into the carrier, the tight fit of the robot arm base and carrier make it difficult for a single user to subsequently rotate the robot arm base relative to the carrier. The supporting features enable the user to partially insert the robot arm base into the carrier without first rotationally aligning the robot arm base and the carrier. Once the supporting features are engaged, the attachment structure bears part of the weight of the robot arm. At this stage, it is more comfortable for the user to rotationally align the robot arm base and carrier, which is permitted by the supporting features. Following the rotational alignment, the user inserts the robot arm base fully into the carrier as previously described.

FIG. 5 illustrates an example in which the robot arm base supporting features are a set of spring ball bearings 516a, 516b, 516c. In FIG. 5, there are three spring ball bearings, however in other examples there may be more than or fewer than three spring ball bearings. The spring ball bearings are exposed at the exterior surface of the robot arm base. The spring ball bearings are arranged in an annulus centred on the longitudinal axis of the robot arm base 510. The annulus lies on a plane which is perpendicular to the longitudinal axis of the robot arm base 510. The spring ball bearings are arranged asymmetrically around the annulus. Each spring ball bearing is moveable in a direction perpendicular to the longitudinal axis of the robot arm base.

In the example of FIG. 5, the carrier supporting feature is a groove 520 on the interior surface of the carrier. The groove is an annulus centred on the longitudinal axis 204 of the carrier. The annulus lies on a plane which is perpendicular to the longitudinal axis of the carrier. The groove is located towards the end of the carrier which first receives the robot arm base. In the example of FIG. 5, the groove is located on the inside edge of the carrier ring 506. The groove 520 may comprise detents 518a, 518b, 518c. These detents are arranged in the same pattern around the groove as the spring ball bearings are arranged around the annulus of the robot arm base. The spring ball bearings and detents are only aligned in one relative orientation of the robot arm base and carrier. The relative positions of the spring ball bearings 516 and the detents 518 are such that, when the spring ball bearings 516 are aligned with the detents 518, the robot arm base is rotationally aligned with the carrier. In other words, when the supporting features are aligned, the rotational alignment features are also aligned. Thus, the supporting features are also rotational alignment features.

The groove is configured to receive the spring ball bearings 516 of the robot arm base. The spring ball bearings 516 spring into, and are retained by, the groove 520. The engagement of the spring ball bearings and groove is sufficient to bear a portion of the weight of the robot arm. The spring ball bearings 516 are permitted to move circumferentially within the groove whilst the spring ball bearings 516 and groove 520 are engaged. Thus, the user may insert the robot arm base into the carrier until the spring ball bearings 516 and groove 520 engage. Once relieved of a portion of the weight of the robot arm, the user then rotates the robot arm base relative to the carrier. When the robot arm base and carrier are rotationally aligned, the spring ball bearings 516 spring into the detents 518. This may provide an audible click which indicates to the user that the robot arm base and carrier are rotationally aligned. The user may then continue to insert the robot arm base into the carrier as described above.

Once the robot arm base rings are engaged with the carrier rings, the robot arm base and carrier are axially aligned. At this stage a locking mechanism is actuated to constrain the robot arm base from moving axially with respect to the carrier. The locking mechanism is moveable between an unlocked position, in which it does not constrain the location of the robot arm base along the carrier's longitudinal axis, and a locked position, in which it does constrain the location of the robot arm base along the carrier's longitudinal axis.

Figure 6:
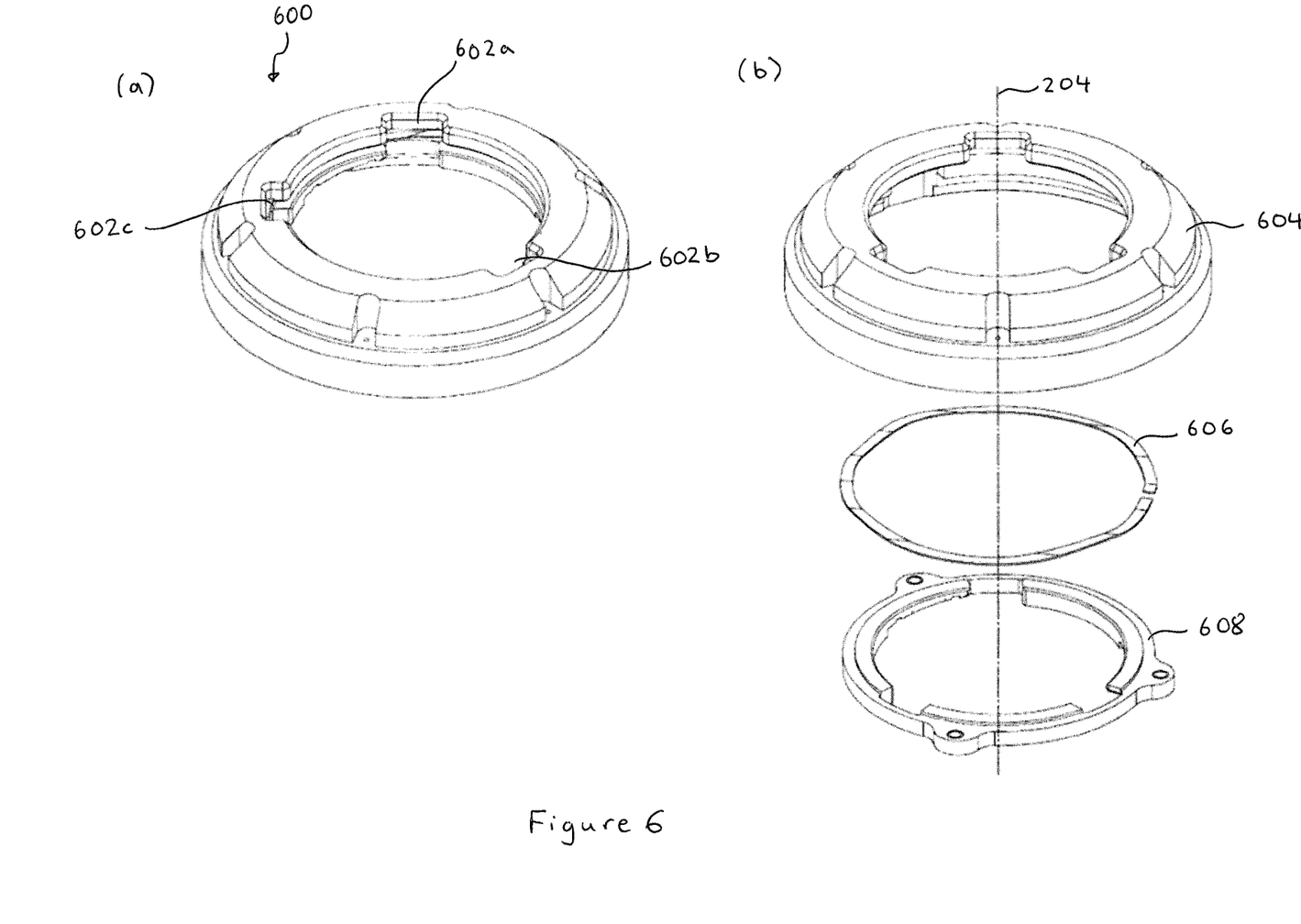
FIGS. 6a and 6b illustrate a locking mechanism.

An exemplary locking mechanism is illustrated in FIG. 6a. An exploded view of the same locking mechanism is shown in FIG. 6b. The locking mechanism comprises a collar 600. The collar 600 is located at the end of the carrier which first receives the robot arm base. The collar is annular. The collar is rotatable about the carrier's longitudinal axis 204. Rotating the collar in one rotational direction actuates it from the unlocked position to the locked position. Rotating the collar in the opposing rotational direction actuates it from the locked position to the unlocked position. The rotation angle between the unlocked position and the locked position may be between 20° and 90°. The rotation angle between the unlocked position and the locked position may be between 30° and 70°. The rotation angle between the unlocked position and the locked position may be between 40° and 50°. The rotation angle between the unlocked position and the locked position may be 45°.

The collar is shaped such that the robot arm base can be inserted into the carrier, and the rotational alignment features and axial alignment features engaged, without actuating the collar. Engaging the robot arm base and the carrier is a separate mechanism to the locking mechanism. These two mechanisms are independent. The two mechanisms are unconnected. In the collar depicted in the figures, the internal radius of the collar is greater than or the same as the internal radius of the carrier. This enables most of the robot arm base to be inserted into the carrier without contacting the collar. The collar 600 comprises recesses or slots 602a, 602b, 602c which match the number and arrangement of the recesses 300a, 300b, 300c of the carrier. In the unlocked position of the collar, the recesses 602 are aligned with the recesses 300 of the carrier. In the locked position of the collar, the recesses 602 are not aligned with the recesses 300 of the carrier. As the robot arm base is inserted in the carrier in the unlocked position of the collar, the roller bearings 400 of the robot arm base pass through the recesses 602 in the collar and are retained in the recesses 300 in the remainder of the carrier. The collar is then rotated to the locked position. In the locked position, the robot arm base cannot be drawn out of the carrier through the collar since the recesses 602 do not align with the recesses 300. Thus, in the locked position of the collar, the robot arm base is constrained from moving axially relative to the carrier.

The collar may be compressible in the direction of the carrier's longitudinal axis 204. For example, the collar may be in a compressed state in the unlocked position, and an uncompressed state in the locked position. When the collar is compressed, it does not apply force to the robot arm base in the direction of the carrier's longitudinal axis 204. When the collar is uncompressed, it applies force to the robot arm base in the direction of the carrier's longitudinal axis 204 so as to push the robot arm base further into engagement with the carrier. In the example of the figures, the robot arm base rings 512, 514 are pushed further into engagement with the carrier rings 506, 508 as the collar moves from its compressed state to its uncompressed state.

In the example shown in the figures, the collar 600 comprises three component parts: an outer grip part 604, a spring washer 606, and a compression part 608. The outer grip part is rotated by the user to actuate the collar between the unlocked and locked positions. The compression part 608 bears down on the robot arm base. The spring washer 606 is sandwiched between the outer grip part 604 and the compression part 608. All three components are annular, and are constrained to rotate together about the carrier's longitudinal axis 204. The spring washer allows for the compression part to move relative to the outer grip part parallel to the carrier's longitudinal axis 204 as the collar is rotated between the unlocked and locked positions. The spring washer compresses when a sufficiently large force is applied to it. This force may be, for example, 100N over the weight of the robot arm. Such a force would be suitable for the case that the robot arm is mounted downwards into the attachment structure. Utilising a spring washer which requires a large force to be applied to compress it reduces the likelihood that the collar is accidentally moved.

Figure 7:
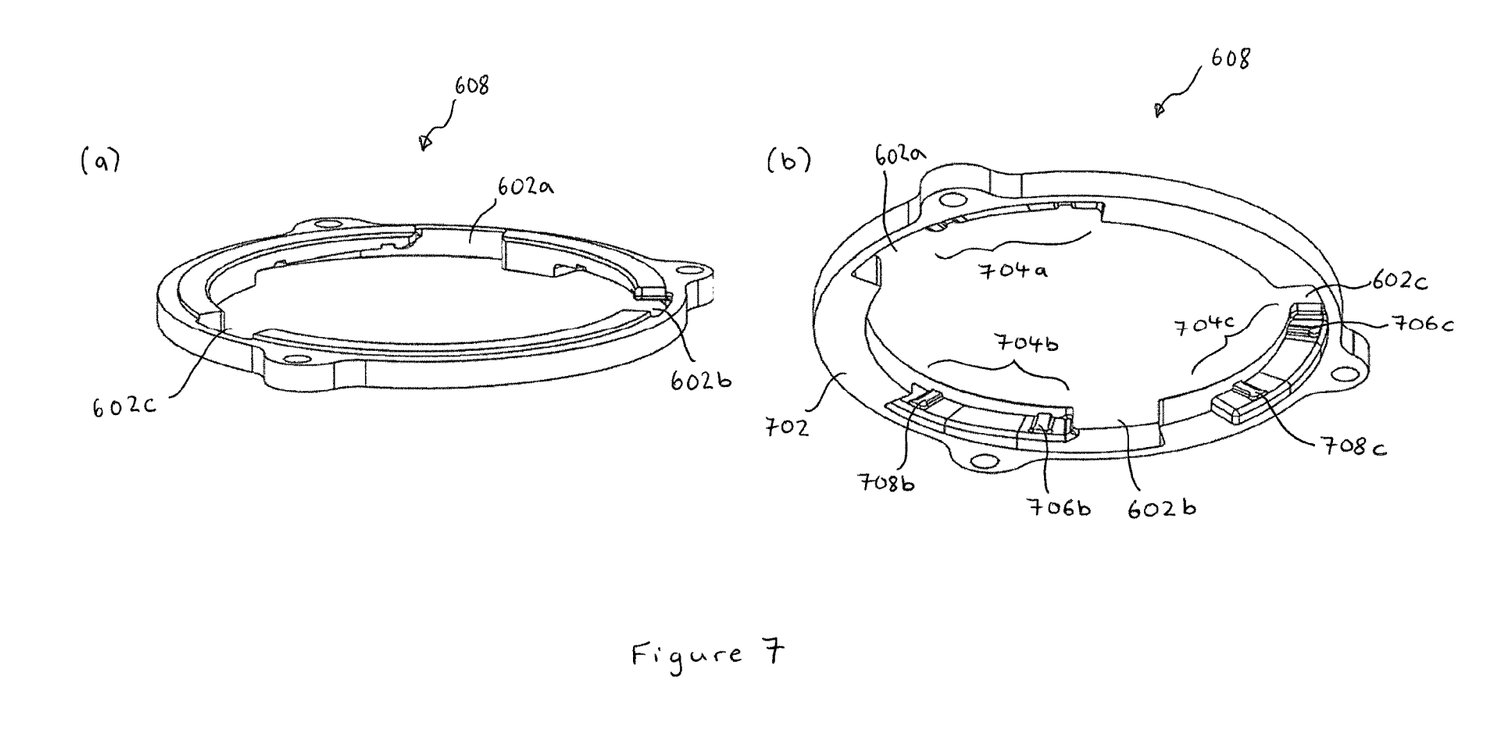
FIGS. 7a and 7b illustrate a compression part of the locking mechanism in more detail.

FIG. 7 illustrates the compression part 608 in more detail. The underside surface 702 of the compression part opposes the outer surface of the outer grip part 604 which the user contacts. The underside surface 702 of the compression part is the face of the collar which contacts the robot arm base when the collar is locked. The underside surface 702 of the compression part 608 is shaped so as to increasingly bear down on the robot arm base as the collar is rotated from its unlocked position to its locked position. The roller bearings 400 of the robot arm base pass through the slots 602. Then, as the collar is rotated, each roller bearing 400a, 400b, 400c contacts a sloped portion 704a, 704b, 704c on the underside surface 702 of the compression part. The sloped portions 704 are sloped around the circumference of the compressed part. One end of the slope is offset in the longitudinal direction of the carrier from the other end of the slope. As the collar is rotated, the slopes 704 cause the compression part 608 to increasingly bear down on the roller bearings 400. Thus, the collar acts to compress the robot arm base against the carrier in the closed position. This prevents any relative movement between the rotational alignment features of the carrier and robot arm base. It also prevents any relative movement between the axial alignment features of the carrier and the robot arm base.

One or more detents may be located on the slopes 704. The figures illustrate an initial detent 706. The initial detent 706 bears down on the roller bearing 400 just after the collar begins to be rotated from the unlocked position. This indicates to the user that the collar operation has begun. The initial detent provides an initial retention. The figures also illustrate a final detent 708. The final detent 708 bears down on the roller bearing 400 just before the rotation of the collar reaches the locked position. The roller bearing 400 having passed over the final detent 708 indicates to the user that the collar operation has finished. The final detent provides full retention. Only the initial detent may be used. Alternatively, only the final detent may be used.

The number and distribution of the slots 602 and slopes 704 matches the number and distribution of the roller bearings 400 of the robot arm.

The outer grip part 604 of the collar may have surface features which enable a user to easily grip and turn it. For example, FIG. 4 illustrates an outer grip part 604 with grooved surface features 404 to aid gripping. Alternatively, the outer grip part 604 may be knurled to aid gripping. FIG. 4 also illustrates a handle 406 which may be utilised to aid rotation of the outer grip part 604 by hand. The handle 406 or other gripping feature may fold out from the collar.

Figure 10:
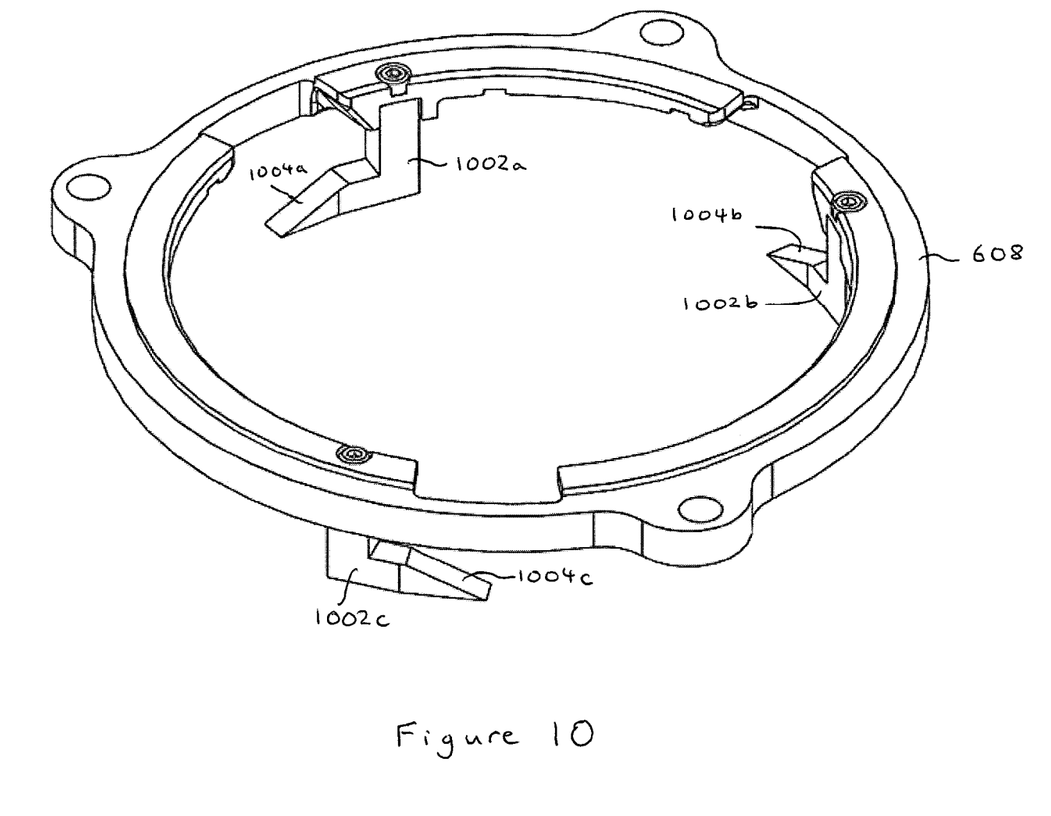
FIG. 10 illustrates a compression part of the locking mechanism.

The collar may further comprise an ejection mechanism to aid removal of the robot arm base from the carrier. The ejection mechanism applies force to the robot arm base in the direction of the carrier's longitudinal axis away from the carrier. This is to prise apart the robot arm base and the carrier. FIG. 10 illustrates an ejection mechanism which is incorporated in the compression part 608 of the collar. The ejection mechanism comprises a set of projections 1002a, 1002b, 1002c. In FIG. 10, there are three projections, each projection adjacent a slot 300. In other arrangements there may be more than or fewer than three projections. The ejection mechanism is configured to prise the robot arm base and carrier apart as the collar is rotated between the unlocked position and an ejected position. The collar is turned in one rotational direction to move between the unlocked position and the locked position. The collar is turned in the opposing rotational direction to move between the unlocked position and the ejected position. When the user is to remove the robot arm base from the carrier, they first rotate the collar from the locked position to the unlocked position. The user then continues rotating the collar in the same direction to rotate the collar from the unlocked position to the ejected position. During this second part of the rotation, the projections lodge underneath the robot arm base, pushing the robot arm base out of the carrier. In the example of FIG. 10, the projections are wedge-shaped. The wedged face 1004a, 1004b, 1004c of each projection of FIG. 10 engages the underside of the roller bearing 400a, 400b, 400c. The wedge shape is such that as the collar is rotated from the unlocked position to the ejected position, an increasing depth of projection is pushed under the roller bearing, thereby causing it to release from the carrier. The rotation between the unlocked position and the ejected position may be up to 5°.

In addition to the rotational alignment features discussed above, the attachment structure may further comprise one or more markings on the exterior of the carrier and or robot arm base for indicating a relative orientation of the carrier and the robot arm base. For example, the carrier and robot arm base may comprise matching markings, which when aligned indicate the carrier and robot arm base to be rotationally aligned with respect to each other. The markings may match in texture, pattern and/or colour.

The carrier may comprise one or more markings which indicate whether the collar is in the locked position or the unlocked position. For example, when the robot arm base and carrier are engaged, the marking may be visible in only one of the locked and unlocked positions. For example, there may be a marking on the portion of the attachment structure which is visible through recesses 602 when the collar has been moved to the locked position. This marking may be a visual marking, such as a coloured and/or patterned marking. There may be one marking visible in the locked position and a different marking visible in the unlocked position.

In order to install the robot arm base into the attachment structure, the user carries out the following steps:
1. The user partially inserts the robot arm base into the carrier until the supporting features of the robot arm base and carrier engage. For example, the user inserts the robot arm base into the carrier until the spring roller bearings 516 engage with the groove 520.
2. The user orients the robot arm base in order to align the rotational alignment features of the carrier and the robot arm base. For example, the user rotates the robot arm base relative to the carrier until the spring roller bearings 516 pop into the detents 518. The user may also align the roller bearings 400 of the robot arm base with the slots 300 of the carrier. The user may also align the raised flat surfaces 504 of the robot arm base with the roller bearings 500, 502 of the carrier in order to aid relative rotational alignment.
3. The user slides the robot arm base into the carrier. As the robot arm base is slid into the carrier, the roller bearings 500, 502 provide support and cantering for the robot arm. The robot arm base is fully inserted into the carrier when the robot arm base ring(s) 512, 514 are engaged with the carrier rings 506, 508, and when the roller bearings 400 of the robot arm base are inserted into the slots 300.
4. The user then rotates the collar 600 to the locked position. If the collar comprises an initial detent, the user may initially rotate the collar to the initial detent position. Once at the initial detent position, the user may reposition themselves if desired. The user then continues to rotate the collar over the final detent to the locked position.

Step 1 is omitted in the case that the robot arm base and carrier do not comprise the optional supporting features.

In other configurations of attachment structure and robot arm base, steps 2 and 3 may be performed in the opposite order to that described above. In other words, the robot arm base and carrier may be axially aligned prior to being rotationally aligned.

The locking mechanism described herein is independent of the mechanism to align and engage the robot arm base with the attachment structure. The locking mechanism is not actuated at all as the robot arm base is rotationally and axially aligned in the attachment structure. Although the locking mechanism comprises a spring which is overcome in order to lock the robot arm base in the attachment structure, that spring does not need to be overcome (either partially or wholly) to align and engage the robot arm base with the attachment structure.

The applicant hereby discloses in isolation each individual feature described herein and any combination of two or more such features, to the extent that such features or combinations are capable of being carried out based on the present specification as a whole in the light of the common general knowledge of a person skilled in the art, irrespective of whether such features or combinations of features solve any problems disclosed herein, and without limitation to the scope of the claims. The applicant indicates that aspects of the present invention may consist of any such individual feature or combination of features. In view of the foregoing description it will be evident to a person skilled in the art that various modifications may be made within the scope of the invention.

The invention claimed is:
1. An attachment structure configured to secure a robot arm to a support structure, the attachment structure comprising:
   a mount configured to mount to the support structure; and
   a carrier configured to connect to the base of the robot arm, the carrier comprising:
      a carrier rotational alignment feature configured to engage a complementary robot arm base rotational alignment feature,
      a carrier axial alignment feature configured to engage a complementary robot arm base axial alignment feature, and
      a locking mechanism moveable, once the robot arm base and the carrier are engaged, between an unlocked position which does not constrain the location of the robot arm base along an axis of the carrier, and a locked position which does constrain the location of the robot arm base along the said axis of the carrier relative to the carrier, wherein the locking mechanism is independent of the carrier rotational alignment feature and the carrier axial alignment feature such that the locking mechanism is not actuated during engagement of the carrier and the robot arm base;
wherein the locking mechanism is compressible between a compressed state in the unlocked position such that no force is applied to the robot arm base by the locking mechanism, and an uncompressed state in the locked position such that force compressing the robot arm base and carrier together is applied to the robot arm base by the locking mechanism.

2. An attachment structure as claimed in claim 1, wherein the carrier comprises a plurality of carrier rotational alignment features configured to engage complementary robot arm base rotational alignment features, wherein the plurality of carrier rotational alignment features are rotationally asymmetric so as to only engage the complementary robot arm base rotational alignment features in one relative rotational configuration of the carrier and robot arm base.

3. An attachment structure as claimed in claim 1, wherein the carrier rotational alignment feature(s) are recesses configured to receive corresponding projections of the robot arm base.

4. An attachment structure as claimed in claim 1, wherein the carrier rotational alignment feature(s) are roller bearings configured to be received in corresponding recesses of the robot arm base.

5. An attachment structure as claimed in claim 1, wherein the carrier comprises a plurality of further carrier rotational alignment features configured to engage complementary further robot arm base rotational alignment features, wherein each further carrier rotational alignment feature is a roller bearing having a rotation axis perpendicular to the carrier's longitudinal axis, and having a roller surface configured to contact the further robot arm base rotational alignment feature so as to aid axial movement of the robot arm base against the carrier during engagement.

6. An attachment structure as claimed in claim 5, wherein the carrier comprises two sets of roller bearings, a first set arranged in a first annulus perpendicular to the carrier's longitudinal axis, and a second set arranged in a second annulus perpendicular to the carrier's longitudinal axis, the first and second annuli being separated in the direction of the carrier's longitudinal axis.

7. An attachment structure as claimed in claim 1, further comprising rotational alignment indicators visible from the exterior of the carrier configured to indicate a relative orientation of the carrier and the robot arm base.

8. An attachment structure as claimed in claim 1, wherein the carrier comprises a plurality of carrier axial alignment features configured to engage complementary robot arm base axial alignment features, the carrier axial alignment feature(s) being rings centred on the carrier's longitudinal axis configured to engage corresponding rings of the robot arm base.

9. An attachment structure as claimed in claim 8, each ring comprising a flange configured to seat a corresponding robot arm base axial alignment feature.

10. An attachment structure as claimed in claim 1, wherein the locking mechanism comprises a collar rotatable about the carrier's longitudinal axis, the collar being compressible in the direction of the carrier's longitudinal axis between a compressed state in the unlocked position such that no force in the direction of the carrier's longitudinal axis is applied to the robot arm base by the collar, and an uncompressed state in the locked position such that force in the direction of the carrier's longitudinal axis compressing the robot arm base and carrier together is applied to the robot arm base by the collar.

11. An attachment structure as claimed in claim 1, wherein the locking mechanism comprises a wing compressible between a compressed state in the unlocked position such that no force transverse to the carrier's longitudinal axis is applied to the robot arm base by the wing, and an uncompressed state in the locked position such that force transverse to the carrier's longitudinal axis is applied to the robot arm base by the wing.

12. An attachment structure as claimed in claim 1, wherein, in the locked position of the locking mechanism, the carrier rotational alignment feature is immovable relative to the robot arm base rotational alignment feature and the carrier axial alignment feature is immovable relative to the robot arm base axial alignment feature.

13. An attachment structure as claimed in claim 10, wherein the face of the collar which contacts the robot arm base is shaped so as to increasingly bear down on the robot arm base as the collar is rotated from its unlocked position to its locked position.

14. An attachment structure as claimed in claim 13, wherein the face of the collar comprises an initial detent and a final detent located such that as the collar begins to be rotated from its unlocked position to its locked position the initial detent bears down on the robot arm base, and the collar reaches the locked position just after the final detent bears down on the robot arm base.

15. An attachment structure as claimed in claim 10, wherein the collar is rotatable about the carrier's longitudinal axis between the unlocked position and an ejected position, the collar further comprising an ejection mechanism configured to apply force to the robot arm base in the direction of the carrier's longitudinal axis prising the robot arm base and carrier apart as the collar is rotated from the unlocked position to the ejected position.

16. An attachment structure as claimed in claim 15, wherein the ejection mechanism comprises one or more wedge-shaped projections which engage one or more complementary robot arm base features.

17. An attachment structure as claimed in claim 10, wherein the collar comprises a marking which is only visible in either the compressed state or the uncompressed state.

18. An attachment structure as claimed in claim 1, wherein the carrier comprises one or more carrier supporting feature configured to engage one or more complementary robot arm base supporting feature.

19. An attachment structure as claimed in claim 18, wherein the carrier supporting feature comprises a groove on an interior surface of the carrier, the groove being in a plane transverse to the longitudinal axis of the carrier.

\* \* \* \* \*